United States Patent [19]

Duranleau

[11] 4,399,233

[45] Aug. 16, 1983

[54] PROCESS FOR PREPARING LOW MOLECULAR WEIGHT OXYGENATED COMPOUNDS FROM SYNGAS USING NOVEL CATALYST SYSTEM

[75] Inventor: Roger G. Duranleau, Georgetown, Tex.

[73] Assignee: Texaco Inc., White Plains, N.Y.

[21] Appl. No.: 357,231

[22] Filed: Mar. 11, 1982

[51] Int. Cl.$^3$ ...................... C07C 27/06; C07C 29/15
[52] U.S. Cl. .................................... 518/701; 518/716
[58] Field of Search ................................ 518/701, 716

[56] References Cited

U.S. PATENT DOCUMENTS 3,940,432  2/1976  Walker et al. ...................... 518/701
4,224,235  9/1980  Beisner et al. ...................... 518/701

*Primary Examiner*—Howard T. Mars
*Attorney, Agent, or Firm*—Carl G. Ries; Jack H. Park; Walter D. Hunter

[57] ABSTRACT

Low molecular weight oxygenated compounds, and particularly ethylene glycol and methanol, are prepared from syngas in good yield by contacting a mixture of carbon monoxide and hydrogen with a catalyst system comprising a rhodium-containing compound, an organic ligand and a sulfonium salt, preferably dissolved in a suitable solvent, and heating the resulting mixture at an elevated temperature and pressure for sufficient time to produce the desired low molecular weight oxygenated compounds, and then recovering the same from the reaction mixture.

24 Claims, No Drawings

PROCESS FOR PREPARING LOW MOLECULAR WEIGHT OXYGENATED COMPOUNDS FROM SYNGAS USING NOVEL CATALYST SYSTEM

BACKGROUND OF THE INVENTION

1. Field of the Invention

This invention relates to a new process for preparing low molecular weight oxygenated compounds. More particularly, the invention relates to an improved process for preparing low molecular weight oxygenated compounds, and particularly ethylene glycol and methanol, from syngas using a novel catalyst system.

Specifically, the invention provides a new and improved process for preparing low molecular weight oxygenated compounds, and particularly ethylene glycol and methanol, from syngas in good yield, which process comprises contacting a mixture of carbon monoxide and hydrogen with a catalyst system comprising a rhodium-containing compound, an organic ligand and a sulfonium salt, preferably dissolved in a suitable solvent, and heating the resulting mixture at an elevated temperature and pressure for sufficient time to produce the desired low molecular weight oxygenated compounds, and then recovering the same from the reaction mixture.

2. Prior Art

Low molecular weight oxygenated compounds, such as ethylene glycol and methanol, are chemicals which have found wide use in industry. Ethylene glycol, for example, is used in the preparation of plasticizers for vinyl polymers and as a component in polyester fibers and antifreeze formulations. Low molecular weight alcohols, such as methanol, find use as solvents and in the production of esters, such as ethyl esters, which can be subsequently used to produce ethylene. In view of these many uses, there is a need to find new and more economical methods for preparing these chemicals.

One proposed method of making ethylene glycol involves the reaction of carbon monoxide with hydrogen in the presence of variously proposed catalyst systems. In general, the mixture of carbon monoxide and hydrogen, commonly known as synthesis gas or syngas, is reacted at elevated temperatures and pressures in the presence of the proposed catalyst. U.S. Pat. No. 2,636,046 discloses the production of ethylene glycol from syngas using a cobalt catalyst. Belgium Pat. No. 793,086 and U.S. Pat. No. 3,940,432 describe the cosynthesis of ethylene glycol and methanol from mixtures of carbon monoxide and hydrogen using a complex rhodium catalyst. U.S. Pat. No. 3,833,634 describes the use of various other metals as catalysts but indicates that only rhodium and cobalt are effective in producing ethylene glycol. Other patents disclosing catalyst systems for converting syngas into polyhydric alcohols are listed in U.S. Pat. No. 4,162,261.

Many of these proposed processes are limited, however, by the nature and activity of the catalyst systems. For example, many of the catalyst systems have poor selectivity as to the production of the desired polyhydric alcohols, or are based on very expensive components. Other catalyst systems have poor solubility in conventional reaction solvents, or have limited solubility with a plating out of the expensive components, such as rhodium, during the reaction.

It is an object of the invention, therefore, to provide an improved process for preparing low molecular weight oxygenated compounds, and particularly ethylene glycol and methanol. It is a further object to provide a new process for preparing ethylene glycol and methanol from syngas using a new catalyst system. It is a further object to provide a new process for preparing ethylene glycol and methanol from syngas which gives good yields and improved selectivity. It is a further object to provide a new catalyst system from producing ethylene glycol and methanol from syngas which has improved solubility in conventional reaction solvents. It is a further object to provide a new process for preparing ethylene glycol and methanol from syngas which avoids the plating out of expensive components, such as rhodium, during the reaction. Other objects and advantages of the invention will appear hereinafter.

SUMMARY OF THE INVENTION

It has now been discovered that these and other objects can be accomplished by the process of the invention comprising contacting a mixture of carbon monoxide and hydrogen with a catalyst comprising a rhodium-containing compound, an organic ligand and a sulfonium salt, preferably dissolved in a suitable solvent, and heating the resulting mixture at an elevated temperature and pressure for sufficient time to produce the desired low molecular weight oxygenated compounds, and then recovering the same from the reaction mixture. It was surprising to find that by the use of the above-noted new catalyst systems one can obtain improved selectivity in the formation of the desired ethylene glycol, and can obtain the said glycol in better yields than obtainable heretofore with many of the related processes. In addition, the new catalyst system has improved solubility in many of the conventional solvents and thus more easily utilized in the reaction. Further, the new process surprisingly avoids the plating out of the expensive catalyst components, such as rhodium, during the reaction and during the product recovery. Further advantage is found in the fact that the process can be operated at moderate temperatures and pressures and avoids the use of extreme conditions required in many of the known processes.

The process of the invention as far as the formation of the desired ethylene glycol is concerned can be represented by the following equation:

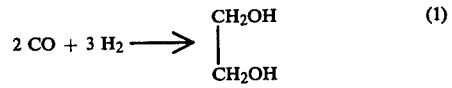

(1)

Typical yields of ethylene glycol based on liquid weight charged range from about 0.9 to about 20%. Other products, besides the ethylene glycol and methanol, include other alcohols, such as ethanol and propylene glycol along with methyl formate with small amounts of dioxolane.

DETAILED DESCRIPTION OF THE INVENTION

In the operation of the process of the invention, the low molecular weight oxygenated compounds, and particularly the ethylene glycol and methanol, are prepared concurrently from a synthesis gas mixture of carbon monoxide and hydrogen by a process comprising the following steps:

(a) contacting the said mixture of carbon monoxide and hydrogen with a catalyst comprising a rhodium-containing compound, an organic ligand and a sulfonium salt, preferably dissolved in a suitable solvent, (b) heating the resulting mixture to an elevated temperature, e.g. at least 150° C., and an elevated pressure, e.g. at least 500 psi, with sufficient carbon monoxide and hydrogen to satisfy the above-noted stoichiometry of the desired ethylene glycol synthesis, until substantial formation of the desired products has been achieved, and (c) preferably isolating the desired products, such as the ethylene glycol and methanol, from the reaction mixture by suitable means, such as fractional distillation.

In order to present the inventive concept of the present invention in the greatest possible detail, the following supplementary disclosure is submitted. The process of the invention is practiced as follows:

As noted, the new catalyst system used in the process of the invention contains a rhodium-containing compound, an organic ligand and a sulfonium salt. The rhodium-containing compound to be used may be chosen from a wide variety of organic or inorganic compounds, complexes, etc. It is only necessary that the compound actually employed contain the rhodium in any state which becomes soluble during the reaction.

The rhodium-containing compound may take many different forms. For instance, the rhodium may be added to the reaction mixture as the salt of an organic acid, such as, for example, rhodium(II) formate, rhodium(II) acetate, rhodium(II) propionate, rhodium(II) butyrate, rhodium(II) valerate, rhodium(III) naphthenate, rhodium(III) acetylacetonate, and the carbonyl or hydrocarbonyl derivatives, such as, for example, tetrarhodium dodecacarbonyl, dirhodium octacarbonyl, hexarhodium hexadecacarbonyl, rhodium tetracarbonyl salts, and substituted carbonyl species, such as rhodium dicarbonyl acetylacetonate.

Preferred rhodium-containing compounds include the rhodium salts of organic carboxylic acids containing up to 10 carbon atoms and the rhodium carbonyls or hydrocarbonyl derivatives. Among these include, for example, rhodium diacetate, rhodium dipropionate, rhodium dicarbonyl acetylacetonate, rhodium(III) acetylacetonate, hexarhodium hexadecacarbonyl and the like, and mixtures thereof.

Any suitable ligand can be used in the catalyst system of the present invention. Examples of those ligands which form complexes or associations with the rhodium-containing compound include, among others, those which contain at least one Lewis base nitrogen atom and/or at least one Lewis base oxygen atom, as well as those which contain elements of phosphorous, arsenic and antimony, and the like. The only requirement is that they form a suitable electronic or ionic association with the rhodium.

Organic ligands which contain at least one Lewis base nitrogen atom preferably contain carbon, hydrogen and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino (—N=), amino, nitrilo, etc. Desirably the Lewis base nitrogen atoms are in the form of imino nitrogen and/or amino nitrogen.

Illustrative examples of the organic nitrogen ligands include, among others, N,N,N',N'-tetramethylehtylenediamine, N,N,N',N'-tetraethylethylenediamine, N,N,N',N'-tetraisobutylmethylenediamine, piperazine, N-methylpiperazine, N-ethylpiperazine, 2-methyl-N-methylpiperazine, 2,2'-dipyridyl, purine, 2-aminopyridine, 2-(dimethylamino)pyridine, 1,10-phenanthroline, methylsubstituted 1,10-phenanthroline, piperidine, 2-methylpiperidine, pyridine, triethylamine, tri-n-butylamine, dibutylamine, methylamine, dodecylamine, morpholine, aniline, benzylamine, octadecylamine, naphthylamine, cyclohexylamine, and the like, and mixtures thereof.

Organic ligands which contain at least one Lewis base oxygen atom preferably contain carbon, hydrogen and oxygen atoms. The carbon atoms can be acyclic and/or cyclic such as aliphatic, cycloaliphatic, aromatic (including fused and bridged) carbon atoms, and the like. Preferably the ligand contains from 2 to 20 carbon atoms. The oxygen atom can be in the form of groups such as hydroxyl (aliphatic or phenolic), carboxyl, etc., the oxygen atom in the hydroxyl group and carboxyl group, etc. being the Lewis base oxygen atom. Such ligands may, of course, contain other atoms and/or groups, such as alkyl, cycloalkyl, aryl, chloro, thiaalkyl, thiaalkylsilyl, and the like.

Illustrative examples of the organic ligands containing oxygen include, among others, glycolic acid, methoxyacatic acid, ethoxyacetic acid, diglycolic acid, thiodiglycolic acid, diethyl ether, tetrahydrofuran, dioxane, tetrahydropyran, pyrocatechol, citric acid, 2-methoxyethanol, 2-n-butanol, 1,2,3-trihydroxybenzene, 2,3-dihydroxynaphthalene, cyclohexane-1,2-diol, oxetane, 1,2,di-methoxybenzene, 1,2-dimethoxybenzene, 1-4 dimechcoybenzene, methyl acetate, ethanol, 1,2-dipropoxyethane, hexane-2,4-dione, 1-phenylbutane-1,3-dione, 3-methylpentane-2,4-dione, the mono- and dialkyl ethers of propylene glycol, of diethylene glycol of dipropylene glycol, and the like, and mixtures thereof.

Illustrative examples of those compounds containing both oxygen and nitrogen include, among others, ethanolamine, diethanolamine, isopropanolamine, N,N-dimethylglycine, iminodiacetic acid, N-methyliminodiacetic acid, N-methyldiethanolamine, 2-hydroxypyridine, 3-hydroxypyridene, 4-hydroxyphridine, picolinic acid, methyl-substituted picolinic acid, nitrotriacetic acid, 2,5-dicarboxypiperazine, N-(2hydroxyethyl)iminodiacetic acid, ethylenediaminetetracetic acid, 2,6)dicarboxypyridine, 8-hydroxyquinoline, cyclohexane-1,2-diamine-N,N,N',N'-tetracetic acid, the tetramethyl ester of ethylenediaminetetracetic acid, and the like, and mixtures thereof.

Coming under special consideration are the Group VB tertiary donor ligands, preferably containing nitrogen, phosphorous, arsenic and antimony. Illustrative examples of this group include, among others, triphenylphosphine, tributylphosphine, triphenylphosphite, triethylphosphite, trimethylarsine, triphenylarsine, tricyclohexylphosphine, trioctylphosphine, dimethylphenylphosphine, triphenylstilbine, trimethylamine, triethylamine, tripropylamine, pyridine, 2,2'-dipyridyl, N,N-dimethylpiperazine, 1,8-bis(dimethylamino)naphthalene and N,N-dimethylaniline.

The above-noted ligands can be combined with the rhodium-containing compound prior to addition to the reaction mixture, or the two components can be added separately. In general, it is preferred to add the two components separately to the reaction mixture.

The promoter to be added to the catalyst system comprises a sulfonium salt. Any suitable sulfonium salt can be used, but the preferred group comprise those of the formula

wherein R is an organic radical, preferably a hydrocarbon or substituted hydrocarbon radical, and X is any suitable anionic group including, among others, anionic groups derived from mineral acids and carboxylic acids. The hydrocarbon radicals represented by R may be any of the aliphatic, hexyl, octyl, dodecyl, octadecyl, cyclohexyl, cyclopentyl, cyclohexenyl, cyclopentadienyl, allyl, 1,6-octadienyl, 2-ethylhexyl, phenyl, 2,4-diemethylphenyl, naphthyl, and the like. Examples of the substituted hydrocarbon radicals include those radicals noted above substituted with 1 or more halogen atoms, and preferably chlorine and bromine, hydroxyl group, alkoxy groups, amino, sulfonyl, and the like groups. Preferred sulfonium salts include those of the above formula wherein R is an aliphatic, cycloaliphatic or aromatic hydrocarbon radical containing up to 20 carbon atoms, and aliphatic, cycloaliphatic or aromatic hydrocarbon radicals containing up to 20 carbon atoms substituted with one or more halogen, OH or alkoxy groups.

Illustrative examples of such sulfonium salts include, among others, trioctylsulfonium bromide, triphenylsulfonium chloride, tricyclohexylsulfonium acetate, tridodecylsulfonium chromate, tri(2,4-dimethylphenyl)sulfonium benzoate, tri(hydroxyphenyl)sulfonium chloride, tri(hydroxyphenyl)sulfonium bromide, tri(chlorophenyl)-sulfonium acetate, tri(methoxyphenyl)sulfonium chloride, tri(methoxycyclohexyl)sulfonium bromide, tri(cyclohexenyl)-sulfonium tetrafluoroborate, tri(2,4-dihydroxyphenyl)sulfonium chromate, tri(3,5-dioctylphenyl)sulfonium chloride and tri(3,5-dimethoxyphenyl)sulfonium acetate.

The particularly preferred sulfonium salts to be used in the new catalyst system comprise the trialkylsulfonium salts, the tricycloalkylsulfonium salts and the triarylsulfonium salts, and such salts substituted on the hydrocarbon radical with from 1 to 3 members of the group consisting of halogen atoms, and particularly chlorine or bromine, hydroxyl group, amino group, alkoxy groups and sulfonyl group, said salts preferably containing no more than 12 carbon atoms.

Coming under special consideration are the triarylsulfonium salts, the tri(alkylaryl)sulfonium salts and their hydroxyl and halogen substituted derivatives. One of the requirements for the salts is that it be stable at the reaction conditions. The triaryl and triaralkyl are the best by far in this regard.

The amount of the rhodium-containing compound to be used in the process may vary over a wide range. The process is conducted in the presence of a catalytically effective quantity of the rhodium-containing compound which gives the desired products in a reasonable yield. The reaction proceeds when employing as little as about $1 \times 10^{-6}$ weight percent, and even lesser amounts of the rhodium-containing compound. The upper concentration is dictated by a variety of factors including catalyst cost, partial pressures of carbon monoxide and hydrogen, operating temperatures, etc. A rhodium-containing compound concentration of from about $1 \times 10^{-5}$ to about 10 weight percent, based on the total weight of the reaction mixture is generally desirable in the practice of the invention.

The amount of the organic ligand to be used in the process of the invention may vary over a wide range depending upon the type of complex to be formed. For example, the amount may vary from that stoichiometric amount needed to form the required complex with the rhodium up to 5 or more times the molar amount needed for the formation of such complexes. Preferably the amount of ligand utilized varies from about 0.5 to about 2.0 moles of ligand per mole of rhodium (contained in the rhodium-containing compound). Ratios outside this range can be employed especially when it is desirable to use diluent quantities of the organic ligand.

A method for determining the optimum amount of the ligand to be used with the rhodium catalyst is disclosed in British Pat. No. 1,565,979, and such pertinent portions of that disclosure is incorporated herein by reference.

The sulfonium salts are generally added to the reaction mixture in amounts varying from about 0.3 to about 2.0 moles for every five atoms of rhodium present. Preferably the salt is added in amounts varying from about 0.8 moles to about 1.6 moles per 5 atoms of the rhodium contained in the catalyst system.

Particularly superior results are obtained when the above-noted three components of the catalyst are employed in a molar basis as follows: rhodium-containing compound 1 to 15 moles to 0.5 moles; organic ligand 0.5 moles to 15 moles; and sulfonium salt 0.5 to 5 moles.

Solvents can and preferably are employed in the process of the invention. As noted above, one of the advantages of the present invention is that the new catalysts are readily soluble in the conventional solvents used in this type of reaction. In general, the preferred solvents are those which are not of the ligand type but which act chiefly to fluidize the catalysts. They are thus preferably substantially inert under the reaction conditions, relatively non-polar and preferably have a boiling point greater than that of the ethylene glycol and other oxygen-containing reaction products so that recovery of the solvent by distillation is facilitated.

Suitable solvents include the liquid hydrocarbons, which can be aliphatic, cycloaliphatic or aromatic, such as, for example, benzene, toluene, xylene, heptane, dodecane, cyclohexane, and the like, and mixtures thereof. Other suitable solvents include the ethers which may be cyclic, acyclic, and heterocyclic materials. Examples of these include isopropyl propyl ether, diethylene glycol dibutyl ether, tetraethylene glycol dimethyl ether, tetraethylene glycol dibutyl ether, diphenyl ether, heptyl phenyl ether, anisole, tetrahydrofuran, 1,4-dioxane and the like, and mixtures thereof. Other suitable solvents include the sulfones, such as tetramethylene sulfone (sulfolane) and the like. Coming under special consideration are the dialkyl ethers of alkylene glycols and the dialkyl ethers of poly(alkylene glycols).

Less preferred solvents include the alcohols, such as cyclohexanol, 2-hexanol, 2-ethylhexanol, 2-octanol, neopentanol, and the like. Also less preferred are the liquid esters which may be aliphatic, cycloaliphatic or aromatic carboxylic acid esters, such as methyl benzoate, butyl cyclohexanoate, dimethyl adipate, dibutyl succinate, and the like, and mixtures thereof.

The amount of the solvent employed may vary as desired. In general, it is desirable to use sufficient solvent to fluidize the catalyst system. In general, this may vary from about 0.3 moles to 100 moles per mole of rhodium.

The temperature range which can be employed in the process of the invention may vary over a considerable range depending upon experimental factors, including the choice of catalyst, pressure and other variables. A preferred range of operability is from about 170° C. to about 350° C. when superatmospheric pressures of syngas are employed. A narrower range of about 170° C. to about 290° C. represents a particularly preferred temperature range.

The pressure employed may also vary over a considerable range, but in most cases is at least above 500 psi. A preferred operating range varies from about 1000 psi to about 15,000 psi, although pressures above 15,000 psi also provide useful yields of the desired product. Particularly preferred pressure ranges vary from about 1000 psi to about 8500 psi. The pressures referred to herein represent the total pressure generated by all the reactants, although they are substantially due to the carbon monoxide and hydrogen fractions.

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether, alkanols, such as methanol, and the like.

In all these synthesis in order to achieve a high degree of selectivity the amount of carbon monoxide and hydrogen present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The desired products of the reaction, e.g. ethylene glycol and methanol, will be formed in significant quantities. Generally the ethylene glycol will be formed in amounts varying from about 0.8% to about 20% by weight of material charged in the specified amount of time. Also formed will be amounts of other lower oxygenated products, such as ethanol, acetic acid, etc. The desired ethylene glycol and methanol can be recovered from the reaction mixture by conventional means, e.g. fractional distillation in vacuo.

The novel process of the invention can be conducted in a batch, semi-continuous or continuous manner. The process is preferably conducted in a batch manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), infrared (ir) mass spectometry, nuclear magnetic resonance (nmr) and elemental analyses, or a combination of these techniques. Analyses have, for the most part, been by parts by weight; all temperatures are in degrees centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates the preparation of ethylene glycol and methanol by the process of the invention.

Into a glass liner, designed to fit into a stainless steel rocking autoclave, was added 0.1658 g (0.75 mmole) of rhodium diacetate, 0.2375 g (2.5 mmole) 2-hydroxypyridine, 0.075 mmole of tris-(4-hydroxyphenyl)sulfonium chloride and 19.0 g (0.082 moles) of tetraethylene glycol dimethyl ether. The resulting suspension was placed in the autoclave, sealed and flushed with 1:1 $CO/H_2$, then pressured with this gas mixture to 3,000 psi, while rocking at room temperature. The temperature was then gradually increased to 220° C. and stabilized. The system was then pressurized to 8,500 psi and repressured periodically over a 18 hour span as it dropped to 8,200 psi. The system was then dismantled after cooling and relieved of pressure. The off gas sample was collected. A weight gain of 0.6843 g was observed. The contents of the liner recovered were found to have 5.65% ethylene glycol, 5.03% methanol along with a small amount of ethyl alcohol,

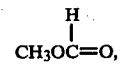

2-hydroxypyridine and triethylene glycol dimethyl ether.

During the reaction there was complete solution of the reactants and catalyst, and there was no evidence of any plating out of the rhodium compound.

EXAMPLE I (Comparative Test)

Example I was repeated with the exception that the reaction was conducted in the solvent without the tris-(4-hydroxyphenyl)sulfonium chloride. The recovered sample showed no weight gain and brown and black solids were dispersed in the liquid layer recovered. In addition, a rhodium mirror and a layer of undissolved solids covered the immersed portion of the liner. A g.c. analysis showed the liquid to contain 0.69% glycol and 0.88% methanol.

EXAMPLE II

Example I was repeated with the exception that the rhodium compound was rhodium dicarbonyl acetylacetonate 0.1935 g (0.75 mmole) and the reaction was conducted for 16 hours. All other conditions and reactants were identical. The liquid product was completely homogeneous (no undissolved solids) and a weight gain of 3.19 g was observed. The solution was found to contain (by g.c. analysis) ethylene glycol 8.03%, methanol 10.4%, methyl formate 1.3%, ethanol 0.37% and tetraethylene glycol dimethyl ether 77.85%. Analysis of the solution by atomic absorption revealed that 97.5% of the rhodium was recovered.

EXAMPLES III to XII

A series of reactions were conducted using tris-(4-hydroxyphenyl)sulfonium chloride as the promoter, as the ratio between the halide and the rhodium compound varied. All the reactions were conducted in the equipment described in Example I employing rhodium III acetylacetonate 0.300 g (0.75 mmole), 2-hydroxypyridine 0.2375 g (2.5 mmole) in tetraethylene glycol dimethyl ether 20.0 g (0.09 moles). The results are shown in Table I. These results demonstrate the productivity increases when the promoter is used. It also shows the improvement in glycol to methanol ratio, and the optimum ratio of rhodium to sulfonium salt promoter.

dimethyl ether 20.0 g (0.09 moles). The results are shown in Table II.

EXAMPLE XXVI

Example I was repeated with the exception that the promoter used was tris-(4-hydroxyphenyl)sulfonium acetate and the rhodium compound was rhodium diacetate. Related results are obtained.

EXAMPLE XXVII

Example I was repeated with the exception that the promoter was tris(4-hydroxyphenyl)sulfonium chloride and the rhodium compound was rhodium diacetate. Related results were obtained.

TABLE I
EFFECT OF TRIS-(4-HYDROXYPHENYL) SULFONIUM CHLORIDE ON THE RHODIUM CATALYZED GLYCOL FROM SYNGAS REACTION
Promotor = tris-(4-hydroxyphenyl) sulfonium chloride

| Example | Millimoles of promoter | $\frac{\text{moles Rh}}{\text{moles promoter}}$ | % $CH_3OH$ | % $(CH_2OH)_2$ | % $CH_3OC(H)=O$ | % $CH_3CH_2OH$ | Weight gain, g | % $CH_4$ in off-gas | % $CO_2$ in off-gas | Solubility |
|---|---|---|---|---|---|---|---|---|---|---|
| III | 0.75 | 1/1 | 1.09 | 0.96 | 0.06 | 0.20 | 0.029 | 0.08 | 3.53 | Complete |
| IV | 0.375 | 2/1 | 1.82 | 2.03 | 0.12 | 0.20 | 0.392 | 0.08 | 3.49 | Complete |
| V | 0.25 | 3/1 | 3.48 | 3.30 | 0.34 | 0.26 | 1.107 | 0.05 | 3.17 | Complete |
| VI | 0.1875 | 4/1 | 2.78 | 3.01 | 0.24 | 0.21 | 1.062 | 0.06 | 3.54 | Complete |
| VII | 0.150 | 5/1 | 2.57 | 3.18 | 0.21 | 0.22 | 1.416 | 0.09 | 3.60 | Complete |
| VIII | 0.094 | 8/1 | 3.99 | 4.69 | 0.38 | 0.23 | 1.5081 | 0.02 | 3.14 | Complete Solution |
| IX | 0.083 | 9/1 | 3.50 | 4.64 | 0.31 | 0.23 | 1.3164 | 0.03 | 4.13 | Complete Solution |
| X | 0.083 | 1/1 | 4.50 | 5.15 | 0.41 | 0.41 | 0.7768 | 0.09 | 2.81 | Complete Solution |
| XI | 0.068 | 11/1 | 2.78 | 3.54 | 0.24 | 0.21 | 0.7691 | 0.13 | 3.95 | — |
| XII | 0.0625 | 12/1 | 3.02 | 3.71 | 0.26 | 0.21 | 0.7275 | 0.11 | 3.25 | Solids |

Temp. = 220° C.
Press. = 8300 psig
Time = 16–18 hrs.

EXAMPLES XIII to XXV

A series of reactions were conducted using tris-(4-hydroxyphenyl)sulfonium bromide as the promoter, as the ratio between the halide and the rhodium compound was varied. All the reactions were conducted in the equipment described in Example I employing rhodium-(III) acetylacetonate 0.300 g (0.75 mmole), 2-hydroxypyridine 0.2375 (2.5 mmole) in tetraethylene glycol

EXAMPLE XXVIII

Examples I to XXVII are repeated with the exception that the ligand employed was 1–10 phenanthroline. Related results are obtained.

EXAMPLE XXIV

Examples I to XXVII are repeated with the exception that the solvent employed was sulfolane. Related results are obtained.

TABLE II
EFFECT OF TRIS-(4-HYDROXYPHENYL) SULFONIUM BROMIDE ON THE RHODIUM CATALYZED GLYCOL FROM SYNGAS REACTION
Promoter = tris-(4-hydroxyphenyl) sulfonium bromide

| Example | millimoles of promoter | $\frac{\text{moles Rh}}{\text{moles promoter}}$ | % $CH_3OH$ | % $(CH_2OH)_2$ | % $CH_3OC(H)=O$ | % $CH_3CH_2OH$ | Weight gain, g | % $CH_4$ in off-gas | % $CO_2$ in off-gas | Solubility |
|---|---|---|---|---|---|---|---|---|---|---|
| XIII | 0.75 | 1/1 | 2.2 | 0.95 | 0.13 | 0.64 | 0.900 | 0.23 | 4.26 | hazy |
| XIV | 0.375 | 2/1 | 2.6 | 1.6 | 0.19 | 0.35 | 0.564 | 0.11 | 3.4 | hazy |
| XV | 0.25 | 3/1 | 3.9 | 3.9 | 0.35 | 0.39 | 1.840 | 0.07 | 2.87 | clear |
| XVI | 0.1875 | 4/1 | | 4.34 | 0.38 | 0.35 | 0.914 | 0.09 | 2.51 | clear |
| XVII | 0.150 | 5/1 | 4.2 | 4.35 | 0.41 | 0.36 | 2.06 | 0.03 | 3.28 | clear |
| XVIII | 0.1250 | 6/1 | 4.0 | 4.24 | 0.37 | 0.37 | 0.56 | — | 5.13 | clear |

TABLE II-continued
EFFECT OF TRIS-(4-HYDROXYPHENYL) SULFONIUM BROMIDE ON THE RHODIUM CATALYZED GLYCOL FROM SYNGAS REACTION
Promoter = tris-(4-hydroxyphenyl) sulfonium bromide

| Example | milli-moles of promoter | moles Rh / moles promoter | % $CH_3OH$ | % $(CH_2OH)_2$ | % $CH_3OC(H)=O$ | % $CH_3CH_2OH$ | Weight gain, g | % $CH_4$ in off-gas | % $CO_2$ in off-gas | Solubility |
|---|---|---|---|---|---|---|---|---|---|---|
| XIX | 0.107 | 7/1 | 5.0 | 5.69 | 0.58 | 0.46 | 2.40 | 0.06 | 2.99 | clear |
| XX | 0.094 | 8/1 | 4.4 | 4.42 | 0.48 | 0.36 | 1.29 | 0.08 | 4.08 | clear |
| XXI | 0.083 | 9/1 | 2.59 | 3.61 | 0.20 | 0.28 | 0.770 | 0.09 | 2.81 | clear |
| XXII | 0.075 | 10/1 | 5.2± | 5.70 | 0.56 | 0.41 | 0.093 | 0.08 | 3.20 | clear |
| XXIII | 0.068 | 11/1 | 4.05 | 4.74 | 0.400 | 0.31 | 1.150 | 0.06 | 3.06 | hazy |
| XXIV | 0.0625 | 12/1 | 3.77 | 4.20 | 0.36 | 0.27 | 1.580 | 0.07 | 3.40 | hazy |
| XXV | 0.0375 | 20/1 | 3.01 | 3.76 | 0.22 | 0.34 | 0.841 | 0.09 | 2.91 | hazy |

Temp. = 220° C.
Press. = 8200–8500 psig
Time = 16–18 hrs.
Solvent = Tetraglyme.

What is claimed is:

1. A process for preparing low molecular weight oxygenated products such as ethylene glycol and methanol from syngas which comprises contacting a mixture of carbon monoxide and hydrogen with a catalyst system comprising a rhodium-containing compound, an organic ligand and a sulfonium salt, and heating the resulting mixture at an elevated temperature and pressure for sufficient time to produce the desired low molecular weight oxygenated products.

2. A process as in claim 1 wherein a solvent is added to the reaction mixture.

3. A process as in claim 1 wherein the rhodium-containing compound is selected from the group consisting of rhodium salts of organic carboxylic acids and the rhodium carbonyls and hydrocarbonyl derivatives.

4. A process as in claim 1 wherein the ligand is an oxygen-containing ligand.

5. A process as in claim 1 wherein the ligand is a nitrogen-containing ligand.

6. A process as in claim 1 wherein the sulfonium salt has the formula $$(R_3S)^+X^-$$

wherein R is an organic radical and X is an anionic group derived from a mineral or carboxylic acid.

7. A process as in claim 1 wherein the sulfonium salt is a member of the group consisting of trialkylsulfonium salts, tricycloalkylsulfonium salts, triarylsulfonium salts, tri(alkylaryl)sulfonium salts and the foregoing salts substituted on the hydrocarbon radical with from 1 to 3 halogen atoms, the foregoing salts substituted on the hydrocarbon radical with from 1 to 3 hydroxyl groups, the foregoing salts substituted on the hydrocarbon radical with from 1 to 3 alkoxy groups, and the foregoing salts substituted on the hydrocarbon radical with from 1 to 3 amino groups.

8. A process as in claim 1 wherein the organic ligand is a Group VB tertiary donor ligand.

9. A process as in claim 2 wherein the solvent is an oxygenated hydrocarbon containing up to 12 carbon atoms.

10. A process as in claim 2 wherein the solvent is a dialkyl ether of a poly(alkylene glycol).

11. A process as in claim 1 wherein the process is conducted at a temperature between 170° C. and 350° C.

12. A process as in claim 1 wherein the process is conducted at a pressure between about 1000 psi and 7500 psi.

13. A process as in claim 1 wherein the carbon monoxide and hydrogen are used in a ratio of 5:1 to 1:5.

14. A process as in claim 1 wherein the catalyst components are employed on a molar basis as follows: rhodium-containing compound 1 to 15 moles; organic liquid 0.5 moles to 15 moles; and sulfonium salt 0.5 to 5 moles.

15. A process as in claim 1 wherein the rhodium-containing compound is rhodium diacetate.

16. A process as in claim 1 wherein the rhodium-containing compound is rhodium dicarbonyl acetylacetonate.

17. A process as in claim 1 wherein the organic ligand is 2-hydroxypyridine.

18. A process as in claim 1 wherein the sulfonium salt is tris-(4-hydroxyphenyl)sulfonium chloride.

19. A process as in claim 1 wherein the sulfonium salt is tris-(4-hydroxyphenyl)sulfonium bromide.

20. A process as in claim 1 wherein the sulfonium salt is tris-(4-hydroxyphenyl)sulfonium acetate.

21. A process for preparing ethylene glycol and methanol from syngas which comprises contacting a mixture of carbon monoxide and hydrogen with a catalytic effective amount of a catalyst comprising a soluble rhodium-containing compound, an organic ligand containing an element of the group consisting of oxygen, nitrogen, phosphorous, arsenic and antimony, and a trihydrocarbylsulfonium salt or a substituted tryhydrocarbylsulfonium salt dissolved in a substantially inert solvent, heating the resulting mixture at a temperature between 170° C. and 350° C. at a pressure between 1000 psi and 7500 psi for sufficient time to produce the ethylene glycol and methanol, and then recovering the same from the reaction mixture.

22. A process as in claim 21 wherein the sulfonium salt is a salt of the group consisting of chlorides, bromides, acetate, propionate, chromates and sulfates.

23. A process as in claim 21 wherein the solvent is tetraethylene glycol dimethyl ether.

24. A process as in claim 21 wherein the solvent is a sulfone.

* * * * *

UNITED STATES PATENT AND TRADEMARK OFFICE
CERTIFICATE OF CORRECTION

PATENT NO. : 4,399,233
DATED : August 16, 1983
INVENTOR(S) : Roger G. Duranleau

It is certified that error appears in the above-identified patent and that said Letters Patent are hereby corrected as shown below:

Column 12, line 30, reading "liquid" should read --ligand--.

Signed and Sealed this

First Day of November 1983

[SEAL]

Attest:

GERALD J. MOSSINGHOFF

Attesting Officer

Commissioner of Patents and Trademarks